United States Patent
Scheinowitz et al.

(10) Patent No.: US 10,092,769 B2
(45) Date of Patent: Oct. 9, 2018

(54) APPARATUS FOR NON-INVASIVE THERAPY OF BIOLOGICAL TISSUE USING DIRECTED MAGNETIC BEAMS

(71) Applicant: Aerotel Ltd., Holon (IL)

(72) Inventors: Mickey Scheinowitz, Kfar Saba (IL); Eli Nhaissi, Old Westbury, NY (US); Ely Levine, Tel Aviv (IL); Daniel Giler, Tel Aviv (IL)

(73) Assignee: Aerotel Ltd., Holon (IL)

( * ) Notice: Subject to any disclaimer, the term of this patent is extended or adjusted under 35 U.S.C. 154(b) by 799 days.

(21) Appl. No.: 14/609,017

(22) Filed: Jan. 29, 2015

(65) Prior Publication Data

US 2016/0220838 A1   Aug. 4, 2016

(51) Int. Cl.
*A61N 2/02* (2006.01)
*A61N 2/00* (2006.01)

(52) U.S. Cl.
CPC .............. *A61N 2/02* (2013.01); *A61N 2/004* (2013.01)

(58) Field of Classification Search
CPC ............................................. A61N 2/00–2/12
See application file for complete search history.

(56) References Cited

U.S. PATENT DOCUMENTS

| | | | |
|---|---|---|---|
| 4,764,743 A | 8/1988 | Leupold et al. | |
| 5,170,784 A | 12/1992 | Ramon et al. | |
| 5,527,352 A | 6/1996 | Vona | |
| 5,691,325 A | 11/1997 | Sandyk | |
| 5,697,285 A | 12/1997 | Nappi et al. | |
| 5,885,976 A | 3/1999 | Sandyk | |
| 6,167,313 A | 12/2000 | Gray et al. | |
| 6,200,259 B1 | 3/2001 | March | |
| 7,610,092 B2 | 10/2009 | Cowan et al. | |
| 8,396,566 B2 | 3/2013 | Kassab et al. | |
| 2004/0267153 A1 | 12/2004 | Bergethon | |
| 2005/0222625 A1 | 10/2005 | Laniado et al. | |
| 2009/0156884 A1* | 6/2009 | Schneider | A61N 2/02 600/14 |

(Continued)

OTHER PUBLICATIONS

Michael J. Caruso et al., "A New Perspective on Magnetic Field Sensing", Honeywell, Inc., May 1998.

(Continued)

*Primary Examiner* — Thaddeus Cox
(74) *Attorney, Agent, or Firm* — Ostrager Chong Flaherty & Broitman PC

(57) ABSTRACT

A system and a method for therapeutic treatment of biological tissue using weak magnetic fields. In accordance with one embodiment, the system comprises: a magnetic field transducer for transducing electrical currents into magnetic fields; a sheet or disk made of high-permeability material and disposed on one side of the magnetic field transducer, but removable therefrom; and a current source coupled to the magnetic field transducer for supplying electrical current thereto. A magnetic beam produced by the interaction of the sheet of high-permeability material with a magnetic field produced by the magnetic field transducer has a profile which is a function of the composition, geometry and thickness of the high-permeability material. Preferably the high-permeability material has a relative permeability value greater than 10,000.

19 Claims, 12 Drawing Sheets

(56) References Cited

U.S. PATENT DOCUMENTS

| | | | |
|---|---|---|---|
| 2009/0203955 A1* | 8/2009 | Klang | A61N 2/02 600/15 |
| 2010/0185042 A1* | 7/2010 | Schneider | A61N 2/004 600/13 |
| 2011/0015555 A1* | 1/2011 | Anderson | A61F 5/0111 602/2 |
| 2011/0306819 A1 | 12/2011 | Jacobson et al. | |
| 2011/0319700 A1* | 12/2011 | Schneider | A61N 2/02 600/13 |
| 2012/0206226 A1* | 8/2012 | Lee | H01F 7/10 335/229 |
| 2016/0238670 A1* | 8/2016 | Shikama | H01L 43/02 |

OTHER PUBLICATIONS

Valery I. Rudnev, "An Objective Assessment of Magnetic Flux Concentrators", Heat Treating Progress, Nov./Dec. 2004, pp. 19-23.

V. Leschynsky et al., "Layered alloys for Effective Magnetic Flux Concentration in Induction Heating", Materials Science-Poland, vol. 25, No. 2, 2007, pp. 275-281.

Fei Sun et al., "Static Magnetic Field Concentration and Enhancement Using Magnetic Materials with Positive Permeability", Progress in Electromagnetics Research, vol. 142, pp. 579-590, 2013.

Fei Sun et al., "DC Magnetic Concentrator and Omni-Directional Cascaded Cloak by Using Only One or Two Homogeneous Anisotropic Materials of Positive Permeability", Progress in Electromagnetics Research, vol. 142, pp. 683-699, 2013.

\* cited by examiner

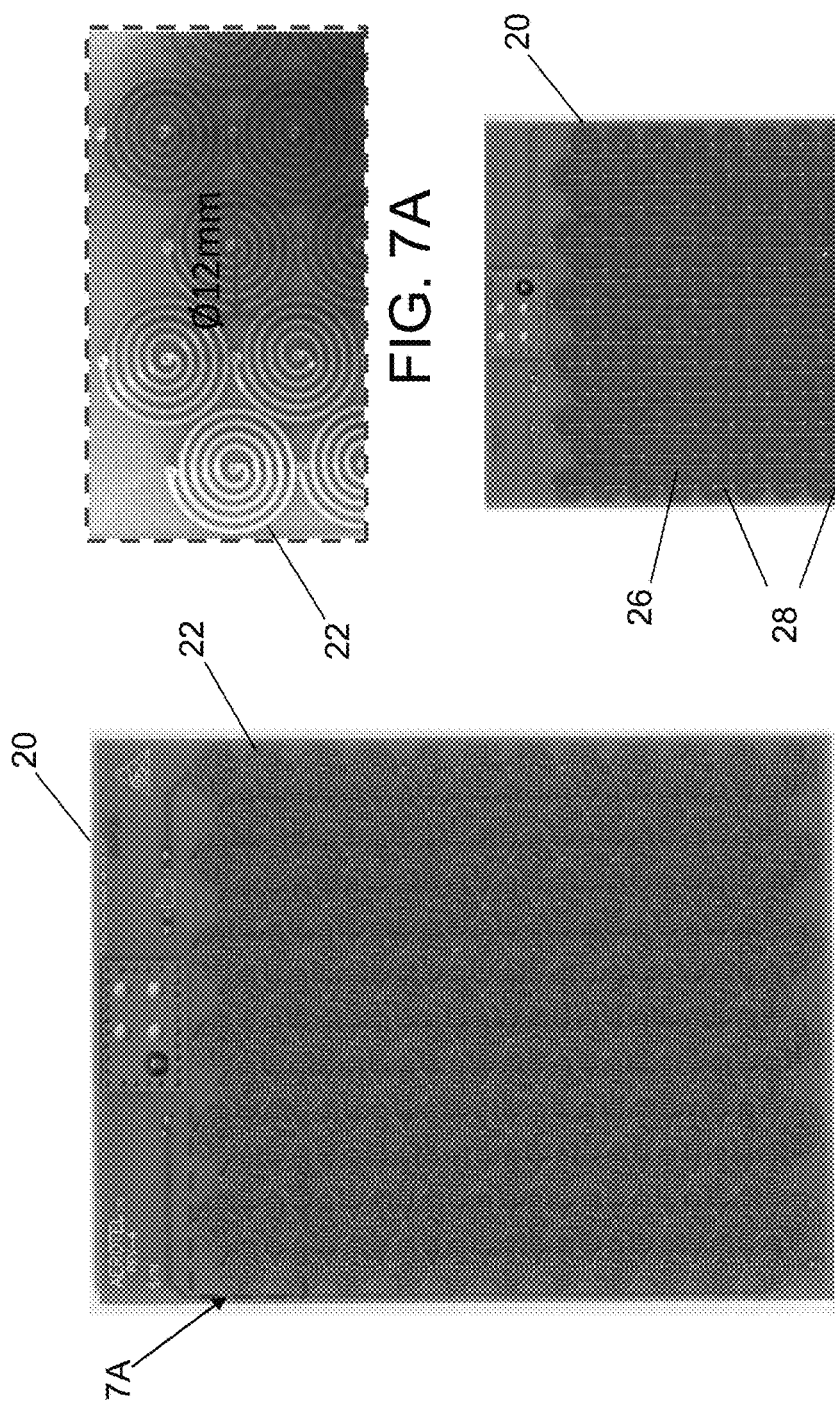

APPARATUS FOR NON-INVASIVE THERAPY OF BIOLOGICAL TISSUE USING DIRECTED MAGNETIC BEAMS

BACKGROUND

The present disclosure relates generally to the treatment of patients having treatable medical conditions using weak (i.e., low-intensity) low-frequency (i.e., several Hz) magnetic fields (WMF). More particularly, this disclosure relates to using WMF to apply therapy in a target volume of biological tissue, such as a tumor or a heart afflicted with arrhythmia.

In the past, the possibility of treating cardiac arrhythmias with the application of WMF has been proposed. In particular, the concept of using a magnetic field generator as a regulator of atrial fibrillation has been previously disclosed. It is now accepted that the effect of a magnetic field on an excitable cell's membrane works through influencing the kinetics of potassium ions. This happens in the neurons as well as in the cardiac myocytes (cardiac muscle cells), which generate the electrical impulses that control the heart rate. Field intensity and modulation frequency have been shown to be important determinants in WMF causing cellular $K^+$ efflux. The $K^+$ channel modifies other ion transporters, such as the calcium and sodium channels. Magnetic fields induce movements of $K^+$ ions across the cell membrane, which affects the shifts of $K^+$ ions through openings in their membrane channels.

Among the diverse excitable cells within the heart are the highly specialized pacemaker cells in the SA node and the AV node, which have spontaneous depolarization due to slow outward efflux of $K^+$ ions until reaching the threshold of excitation. Atrial cells and ventricular cells have different electrophysiological properties, yet both possess $K^+$ channels (in addition to $Na^+$ and $Ca^{2+}$ channels). But, in a pathological state, they may exhibit an automatic excitability to fire rapidly or irregularly, causing cardiac arrhythmias. This is one mechanism of cardiac arrhythmia.

A WMF (as weak as is still capable of affecting the flux of $K^+$ ions across the cell membranes) can ignite a self-propagated process of $Ca^+$, $K^+$ and $Na^+$ ion shifts. It depends on the modes of WMF stimulation (frequency, intensity and configuration) and/or an additional external intervention (such as the application of drugs), to determine if the cell will discharge following its excitation or be further inhibited. It is known from in vitro experiments that WMF can induce activation, reactivation and inhibition of the excitable cells. Weak magnetic fields can have a negative chronotropic effect on cardiac pacemaker cells and can be used continuously or intermittently to alleviate atrial fibrillation.

In order to facilitate non-invasive therapy of target organs (such as the heart) or localized regions inside the human body (such as a tumor), it is important that the magnetic field be concentrated or focused at the area requiring treatment. U.S. Pat. No. 8,396,566 discloses the use of spiral coils to generate magnetic fields for the purpose of resynchronizing a heartbeat. U.S. Published Patent Application No. 2005/0222625 discloses a coil array forming part of a non-invasive pacemaker. Although these references disclose that focused magnetic fields can be directed toward a target site in a heart (such as the SA node, the atria, the left ventricular septum, etc.) to provide non-invasive therapy, neither reference discloses any mechanism or means for directing and focusing the magnetic field to form a magnetic beam.

Accordingly, there is a need for apparatus for directing and focusing magnetic fields at a target site inside biological tissue.

SUMMARY

The subject matter disclosed in detail below relates to non-invasive treatment of biological tissue (e.g., a node of a heart or a tumor) by applying magnetic fields (or magnetic flux) in the form of a focused beam directed at into target tissue/organ. In the case of patient therapy, magnetic fields can be generated by an array of thin coils (spirals), activated by electric currents, which are printed on a flexible pad attached to a portion the patient's anatomy. The apparatus (disclosed in detail below) is capable of converging a wide magnetic beam into a narrow magnetic beam and directing the latter toward specific areas of the patient's body in accordance with specified medical protocols. The magnetic fields induce potential differences in the target tissue/organ. The convergence of the magnetic beam (and associated electromagnetic induction) is achieved by inserting a sheet made of high-permeability materials in front of the coil array. Different structures and/or shapes and/or thicknesses of the high-permeability sheets produce different convergence and/or different pointing or focusing of the electromagnetic induction. For example, the thickness of the high-permeability sheet may be constant or may vary linearly or non-linearly.

In accordance with some embodiments for applying non-invasive therapy at a target site inside a human body, a sheet or disk made of high-permeability material is placed in front of the coil array for focusing magnetic induction into a confined beam that penetrates into the human body. This enables treatment of a specific target inside the human body. The magnetic induction is modulated at very low frequencies (i.e., tens of Hz). Thus it can be categorized and considered as a static field.

In accordance with the implementations disclosed in detail below, the magnetic flux is created by a plurality of thin coils (e.g., spirals having any one of a plurality of different geometries), arranged in some array form (e.g., rows and columns or along diagonals), and printed on a flexible plastic pad. The coils are connected together and to a current source. An array of coils on a pad will hereinafter be referred to as a "coil pad". When the coil pad is properly placed adjacent to the patient, some magnetic induction profile appears in the vicinity and inside the portion of the patient's body which is being treated.

A major limitation of some known medical procedures is the fact that the spatial distribution of the magnetic field is fixed, although the intensity of the magnetic field can be governed by the value of the current. In the systems disclosed herein, the magnetic fields can be pointed toward specific regions of the human body and the penetration depth of the magnetic beam is controlled.

In accordance with embodiments disclosed in detail below, the pointing or convergence of the magnetic beam is done by placing a sheet or disk made of high-permeability material in front of a coil pad. In the vicinity of such a high-permeability material, the magnetic flux is concentrated and thus can be deflected in accordance with the composition, thickness, geometry, and position (relative to the coils) of the high-permeability material.

The high-permeability sheet or disks can be designed once at the factory level for any specific angle of deflection. For example, when a coil pad and a high-permeability sheet are placed adjacent to a patient, a magnetic field can be directed at a specified target volume within the patient's body. The physician can choose the appropriate high-permeability sheet (each sheet is designated with a specific direction or with the name of a specific part of the body). Without any specific limitation, one can assume that the number of high-permeability sheets provided with each treatment unit will be between 8 and 16. The sheets in inventory may have different geometries, different compositions, and/or different thicknesses. For different therapies, one high-permeability sheet having a first composition and/or first configuration can be substituted for another high-permeability sheet having a second composition and/or second configuration. Alternatively, two high-permeability sheets having different compositions and/or different configurations can be used together by overlaying one on the other.

One aspect of the subject matter disclosed in detail below is an apparatus for treatment of patients, comprising: a coil array comprising a multiplicity of coils made of electrically conductive material; a structure made of high-permeability material, the structure being mechanically coupled to the coil array; and a current source electrically coupled to the coils for supplying electrical current to the coils. The location of the high-permeability structure relative to the coil array may be adjustable in X, Y and Z directions. In some implementations, the high-permeability structure is a disk or a sheet. The sheet or disk may have a constant or varying thickness. In one implementation, the coils are spiral coils connected in series and printed on a pad made of flexible plastic material. The high-permeability material preferably has a relative permeability value greater than 10,000 (absolute units) and may comprise a nickel-iron alloy.

Another aspect of the subject matter disclosed below is a method of therapeutically treating biological tissue, comprising the following steps: placing an array of electrically conductive coils near a portion of a patient's body with an intervening structure made of high-permeability material; and supplying the coils with an electrical current sufficient to cause the coils to generate a modulated magnetic field which is altered by the presence of the intervening high-permeability material. Preferably, the modulated magnetic field has a peak intensity less than 10 microTesla (equal to 100 milliGauss) and a frequency of about 16 Hz. The generated magnetic field is strengthened and focused at a particular position with the aid of the high-permeability material. In cardiological applications, the generated magnetic field is focused in a region of the patient's heart. Other applications may include treatment of other parts of the human anatomy, veterinary medicine, three-dimensional tissue culture, and biochemical engineering in a bioreactor.

A further aspect is a system for therapeutic treatment of patients, comprising: a magnetic field transducer for transducing electrical signals into magnetic fields; a first sheet or disk made of high-permeability material, the first sheet or disk being disposed on one side of the magnetic field transducer, but removable therefrom; a second sheet or disk made of high-permeability material, the second sheet or disk being interchangeable with the first sheet or disk; and a current source coupled to the magnetic field transducer for supplying electrical current thereto. When the first sheet or disk is in place, a first magnetic beam having a first profile is produced by the interaction of the first sheet or disk of high-permeability material with a magnetic field produced by the magnetic field transducer. When the second sheet or disk is in place, a second magnetic beam having a second profile is produced by the interaction of the second sheet or disk of high-permeability material with a magnetic field produced by the magnetic field transducer, the first and second profiles being different. Again the high-permeability material has a relative permeability value greater than 10,000 and may be a nickel-iron alloy. In accordance with one embodiment, the location of the sheet or disk made of high-permeability material relative to the magnetic field transducer is adjustable.

Other aspects of systems and methods for treating patients using focused magnetic fields are disclosed and claimed below.

BRIEF DESCRIPTION OF THE DRAWINGS

FIG. 7 is a diagram showing a front side of a flexible coil pad comprising a multiplicity of spiral coils.

FIG. 7A is a diagram showing (on a magnified scale) the portion of the flexible coil pad inside the rectangular area 7A indicated in FIG. 7.

FIG. 8 is a diagram showing a back side of the flexible coil pad depicted in FIG. 7.

Reference will now be made to the drawings in which similar elements in different drawings bear the same reference numerals.

DETAILED DESCRIPTION

In accordance with the illustrative embodiments disclosed herein, magnetic fields are applied to a region of a patient's body (e.g., a heart) using a transducer (e.g., a two-dimensional array of coils) placed adjacent to the patient's body. A magnetic lens made of high-permeability is placed between the transducer and the patient's body for the purpose of strengthening and focusing at a particular location the magnetic field produced by the transducer. In the event of continuous application of pulsed magnetic fields, the transducer will be attached and secured to the patient's body by straps or belts. Upon energization of the coils with electric current, the coils and magnetic lens produce a net magnetic field that can be directed toward a specific target volume inside the patient's body. The apparatus further comprises a current source that provides electrical current with a periodic waveform to the coil array. By way of example, the current may be a direct current or may be alternating with a frequency in a range of 0.1 Hz to 10 kHz. Typically the frequency will be in the range of 4 to 64 Hz. The waveform may be sinusoidal, triangular, trapezoidal, square, or a combination of more than one of these waveforms, i.e., a combination of sinusoidal with trapezoidal or square, and is registered by the apparatus.

In the case of energization of the coils with a sinusoidal current, the current source is operated to output a peak voltage, typically, of 9 V relative to ground. This voltage provides a peak current of 20 µA and up to 0.5 A or more if needed. In accordance with one embodiment, the intensity of the alternating magnetic fields generated is in a range from 0.1 to 10 microTesla, and the frequency is in the vicinity of 16 Hz or any one of its octave-harmonics.

Figure 1:
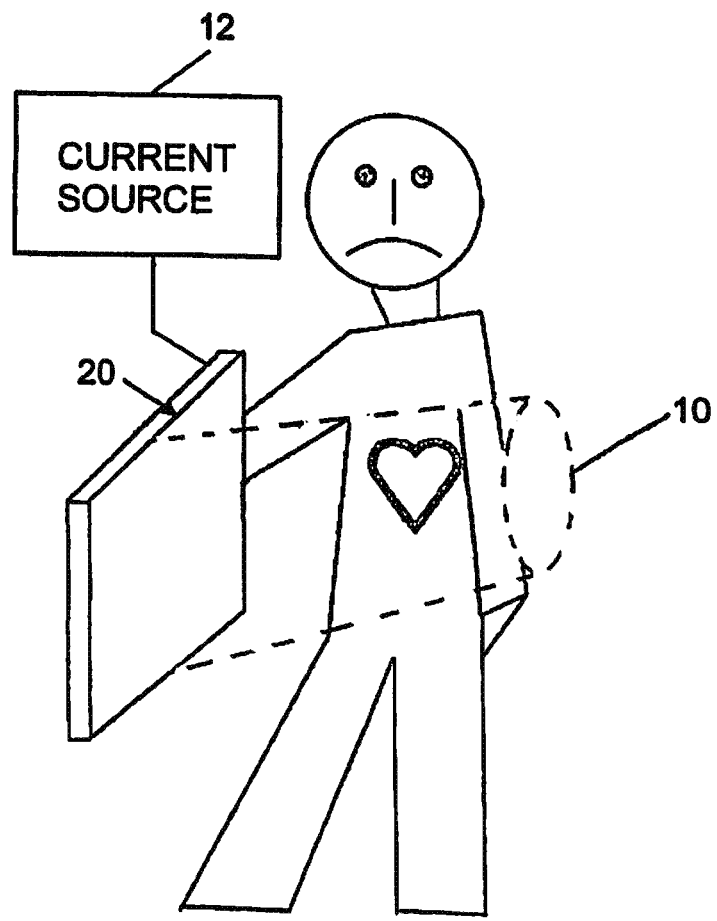
FIG. 1 is a diagram showing a patient's heart being treated with a magnetic field generated by an array of coils incorporated in a flexible pad (coil pad) in accordance with a known method for treating some cardiac ailments. The magnetic beam is wide and covers without discrimination the whole area of the heart. The size of the coil pad can be reduced, in which case a selected portion of the heart can be treated. Although this diagram shows the coil pad separated from the patient, in practice the coil pad will be placed in contact with the patient.

FIG. 1 is a diagram showing a patient's heart being treated with a magnetic field 10 generated by a planar array of coils incorporated in a coil pad 20 in accordance with a known method for treating some cardiac ailments. Although this diagram shows the coil pad 20 separated from the patient, in practice the coil pad 20 will be placed adjacent if not in contact with the patient. The coils of coil pad 20 are energized by a current source 12 which induces electrical signals having selected waveform, intensity and frequency. The intensity of the resulting magnetic field should be less than 10 microTesla, and preferably should be less than 1 microTesla. The current source 12 may have a manually operated input devices (such as rotary knobs or linear slides) for selecting the waveform, intensity and frequency of the WMF to be emitted. In accordance with the embodiment depicted in FIG. 1, the settings of the current source 12 are selected by a system operator via an operator interface (not shown) that interfaces with a computer (not shown). Alternatively, the treatment protocol can be pre-stored in a memory device. During application of the WMF, the effects of the treatment on the heart can be detected using sensors (e.g., ECG electrodes). The signals from those sensors enable the physician to monitor the ongoing therapy.

Figure 2:
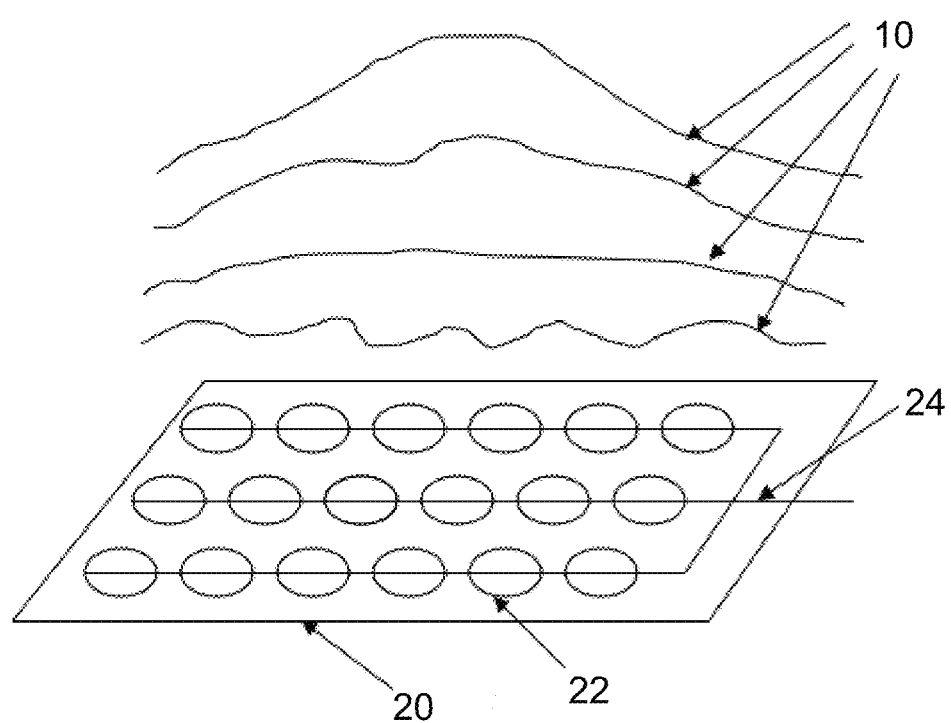
FIG. 2 is a diagram showing the generation of a magnetic field by a coil pad. Each element is energized by electric current and thus generates a respective local magnetic field. The superposition of these local magnetic fields produces a total magnetic field having B-field strength profiles that vary as a function of distance from the pad.

In accordance with one embodiment, the coil pad 20 seen in FIG. 1 may comprise an array of printed spiral coils 22 represented by respective circles in FIG. 2. The coils 22 can be arranged in rows and columns or in staggered rows. All of the spiral coils 22 are connected to the terminals of a current source (not shown) by means of a network of electrical conductors 24. Each coil 22 is energized by electric current and thus generates a respective local magnetic field. The superposition of these local magnetic fields produces a total magnetic field 10 having B-field strength profiles that vary as a function of distance from the coil pad 20.

The apparatus shown at a high level in FIGS. 1 and 2 produces a magnetic field 10 in the form of a beam that is wide and covers without discrimination the whole area of the patient's heart. Alternatively, the size of the coil array incorporated in the coil pad 20 can be reduced, in which case a selected portion of the heart can be treated. It would highly desirable if an improved magnetic wave generator were provided having the capability of deflecting a magnetic beam and directing it toward specific areas of the heart (or other target tissue) in accordance with specified medical protocols. Before disclosing embodiments that accomplish the foregoing, it would be helpful to explain the principles which underlie the focused magnetic wave generation technology disclosed herein.

The general theory of electromagnetic phenomena is based on Maxwell's equations, which constitute a set of four coupled first-order partial-differential equations resulting in the space and time changes of electric and magnetic fields to their scalar source densities (divergence) and vector source densities (curl). For stationary media, Maxwell's equations in the differential form are:

$$\nabla \cdot D(r,t) = \rho(r,t) \text{ (Gauss's electric law)} \quad (1)$$

$$\nabla \cdot B(r,t) = 0 \text{ (Gauss's magnetic law)} \quad (2)$$

$$\nabla E(r,t) = -\partial B(r,t)/\partial t \text{ (Faraday's law)} \quad (3)$$

$$\nabla \times H(r,t) = \partial D(r,t)/\partial t + J(r,t) \text{ (Ampere's law)} \quad (4)$$

Maxwell's equations involve only macroscopic electromagnetic fields and explicitly, only macroscopic densities of free charge $\rho(r, t)$, giving rise to the free current density $J(r, t)$. The effect of the macroscopic charges and current densities bounded to the medium's molecules is indicated by auxiliary magnitudes D and H, which are related to the electric and magnetic fields E and H by the so-called constitutive equations that describe the behavior of the medium. In general, the quantities in these equations are functions of the position (r) and the time (t), with the following definitions: E is the electric field intensity (Volts/meter); H is the magnetic field intensity (Amperes/meter); D is the electric flux density (coulombs/square meter); B is the magnetic flux density (Tesla or weber/square meter); p is the free electric charge density (coulombs/cubic meter); and is the free electric current density (Amperes/square meter).

The magnetic behavior in matter involves another parameter called magnetization M with the following relations:

$$H=B/\mu-M \quad (5)$$

$$M=\chi_m H \quad (6)$$

$$B=\mu_0\mu_r H \quad (7)$$

where $\mu=\mu_0\mu_r$ is the magnetic permeability and $\chi_m$ is the magnetic susceptibility. The human body has very minor magnetic effects. Thus the magnetic nature of the tissues can be neglected. The absolute permeability $\mu_0$ equals $4\pi \times 10^{-7}$ and the relative permeability $\mu_r$ varies from 1 (free space) to a few thousands. Hence, in common materials known as "paramagnetic" materials, in which $\mu_r \gg 1$, amplification or concentration of the magnetic flux B occurs.

Currents which arise due to the motion of charges are the source of magnetic fields. When charges move in a conducting wire and produce a current I, the magnetic field at any point P due to the current can be calculated by adding up the magnetic field contributions dB from small segments of the wire ds. These segments can be thought of as a vector quantity having a magnitude of the length of the segment and pointing in the direction of the current flow. The infinitesimal current source can then be written as I ds.

Let r denote the distance from the current source to the field point P and the corresponding unit vector. The Biot-Savart law gives an expression for the magnetic field contribution from the current source:

$$dB=\mu I ds/4\pi r^2 \quad (8)$$

Applying this law to a current loop with radius R gives the magnetic flux at a distance z along the axis of the loop:

$$B=\mu I R^2/2(R^2+z^2)^{3/2} \quad (9)$$

Applying this law to a solenoid with N turns and total length L gives the magnetic flux in the center of the solenoid:

$$B=\mu NI/L \quad (10)$$

These examples demonstrate that if materials with high permeability are added to current-carrying wires, the magnetic flux will be enlarged or will be concentrated. As used herein, the term "high permeability" means having a relative permeability value greater than 10,000.

Figure 3:
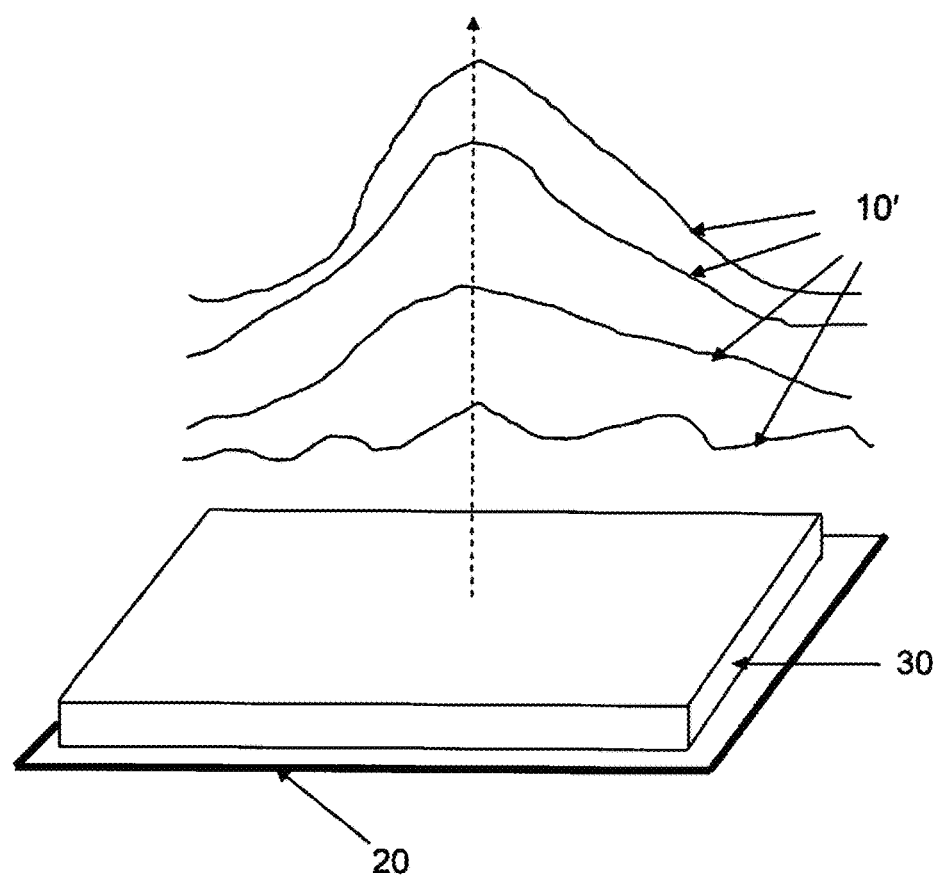
FIG. 3 is a diagram showing the generation of a magnetic field by an apparatus comprising a coil pad that is covered by a flat sheet (e.g., constant thickness) made of high-permeability material, which flat sheet focuses the total magnetic field to form a magnetic beam.

FIG. 3 is a diagram showing the generation of a magnetic field 10' by an apparatus comprising a planar array of coils incorporated in a coil pad 20 that is covered by a sheet 30 made of high-permeability material. In the alternative, the sheet can be replaced by a disk made of high-permeability material, which may cover only a portion of the coil pad 20. In accordance with the embodiment depicted in FIG. 3, the sheet 30 is flat, i.e. has a constant thickness. As indicated by the respective profiles of the magnetic field 10', the high-permeability sheet 30 has the effect of focusing the total magnetic field 10' to form a magnetic beam that is sharper than the beam depicted in FIG. 2 and penetrates to a greater depth. The high-permeability sheet 30 can be designed to change the planar beam produced by the coil pad 20 to any configuration desired in order to penetrate into deep body organs/tissue and by converging the magnetic beam, it enables focus of the therapy on a narrower region or in a smaller target volume.

In accordance with one embodiment, one or more thin sheets or disks of high-permeability material can be placed in front of or attached to the front of the coil pad 20. These materials (known as paramagnetic materials) influence the magnetic fields by attracting the field lines and concentrating the magnetic flux into more confined volume. Paramagnets do not retain any magnetization in the absence of an externally applied magnetic fields, thus the total magnetization will drop to zero when the applied field is removed. The relative value of the permeability dictates how significant the attraction of the field will be.

For high-permeability materials it is recommended to use popular materials known as Permalloys which are available for industrial projects from many manufacturers. Permalloy is a nickel-iron magnetic alloy with 80% nickel content which is notable for its very high magnetic permeability. Commercial Permalloys typically have relative permeability values greater than 10,000, compared to several thousand for ordinary steel. Typical applications of Permalloys include: transformer laminations, relays, recording heads, deflection and focusing of yokes, amplifiers and loudspeakers. For example, Permalloy 80, based on nickel-iron-molybdenum alloy, provides very high initial and maximum magnetic permeabilities and minimal core losses at low field strengths (low coercive force, low hysteresis loss, low eddy-current losses and low magnetostriction). Permalloy 80 has the following composition: 80% Ni, 14.7% Fe, 4.4% Mo, 0.5% Mn, 0.3% Si, 0.1% C. This vacuum-melted product also offers the advantages of small size and weight and can be purchased in sheets having a thickness are a few millimeters.

Another example of relevant material is known by its commercial name as Mu-METAL®, which is commercially available from Magnetic Shield Corporation, Bensenville, Ill. Mu-METAL® is a nickel-iron alloy composed of approximately 77% Ni, 16% Fe, 5% Cu, and 2% Cr or Mo that is notable for its high magnetic permeability. Mu-METAL® typically has relative permeability values greater than 10,000. This product is used primarily in low-intensity fields where high initial permeability and high shielding efficiency are desired. Mu-METAL® is available as stress-annealed (partially annealed for ease of machinability) sheet stock and is used for fabricated shields such as enclosures, cylinders, cans, channels or three-dimensional boxes. Mu-METAL® stress-annealed alloy is available in many forms, but most shields are fabricated in gauges from 0.014" to 0.062" thickness [0.36 to 1.57 mm]. Mu-metal foil is fully annealed and available in stock gauges from 0.002" to 0.010" thickness [0.05 to 0.25 mm].

For the purpose of focusing the field, one may add a sheet of Permalloy or Mu-METAL® material, with a typical thickness of 1-2 mm on top of the coil pad 20 and increase the magnetic flux in front of the coil pad 20 as illustrated in FIG. 3. The specific choice of the material type and the material thickness controls the focusing effect.

Figure 4:
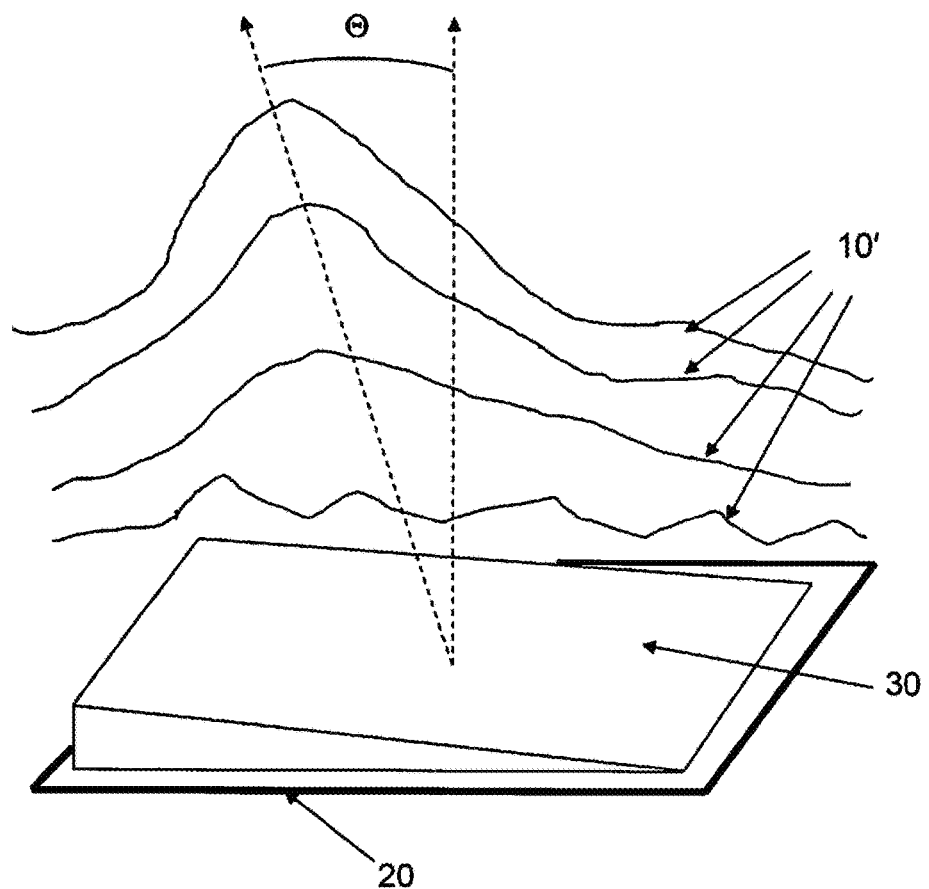
FIG. 4 is a diagram showing the generation of a magnetic field by an apparatus comprising a coil pad that is covered by a sheet having a non-constant thickness (e.g., the thickness varies linearly) and made of high-permeability material, which sheet focuses and deflects the total magnetic field to form a magnetic beam directed in a desired direction.

In accordance with alternative embodiments, the sheet or disk of high-permeability material may have a thickness that varies. FIG. 4 depicts the generation of a magnetic field 10' by an apparatus comprising a coil pad 20 that is covered by a sheet 30 made of high-permeability material and having a thickness that varies linearly in one direction. As indicated by the respective profiles of the magnetic field 10', a high-permeability sheet 30 with linearly varying thickness has the effect of focusing and deflecting the total magnetic field 10' to form a magnetic beam that is displaced relative to the beam depicted in FIG. 3 by an angle Θ. The specific choice of the material structure controls the deflection effect.

The advantages of the focusing and the deflecting are obvious—the treatment can be aimed at specific areas of the cardio-vascular system (or other biological tissue) and optimized for specific procedures.

Figure 5:
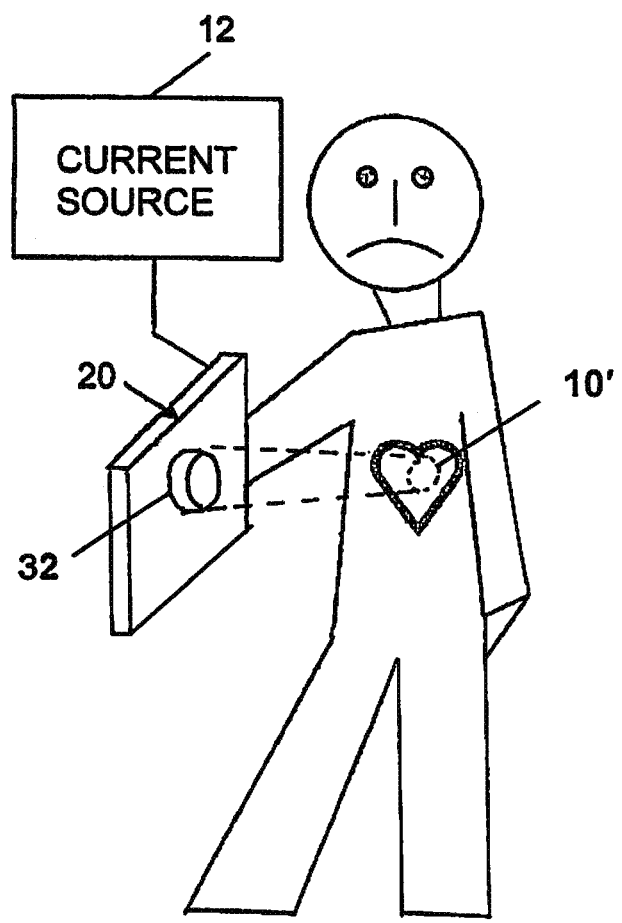
FIG. 5 is a diagram showing a patient's heart being treated with a magnetic field generated by a coil pad that is only partially covered by a magnetic lens made of high-permeability material. The portion of the magnetic beam produced by the coil array and focused by the magnetic lens is narrow and directed toward a specific part of the heart. Although this diagram shows the coil pad and magnetic lens separated from the patient, in practice the magnetic lens may be placed in contact with the patient.

In accordance with a further alternative embodiment shown in FIG. 5, a flexible coil pad 20 may be equipped with a magnetic lens 32 in the form of a disk made of Permalloy or Mu-METAL® material, which disk covers only a portion of the coil array. Such a magnetic lens 32 strengthens and focuses the magnetic field produced in the volume of space adjacent the area of the coil pad 20 which is covered by the lens. A focused magnetic beam 10' is depicted in FIG. 5 to show the field-strengthening and field-focusing effects of such a magnetic lens 32. However, it should be appreciated that portions of the coil pad 20 not covered by the magnetic lens 32 will also produce magnetic fields weaker in strength, which WMF is not depicted in FIG. 5. FIG. 5 illustrates a strengthened and focused portion of the magnetic field, effectively forming a beam for more accurate and specific procedures. The resulting magnetic beam 10' is narrow and directed toward a specific part of the heart (or other human tissue). Although this diagram shows the coil pad 20 separated from the patient, in practice the coil pad 20 will be placed in close proximity to the patient.

The magnetic lens 32 may be sized and shaped and disposed on a selected area of the coil pad 20 to produce a first magnetic field having a specified strength at a first depth in human tissue, while the coils outside that selected area produce a second magnetic field having the same specified strength at a second depth in human tissue, the first depth being deeper than the second depth. This capability is useful in situations where anatomic organs which are geometrically irregular are being treated. For example the "base" of the heart is deeper in the body (or the chest), while the "apex" of the heart is closer to the chest. Therefore if the heart needs to get a certain amount of energy, it should be given homogenously along its surface, despite the heart's surface being at varying distances from the body surface (i.e., measured from the skin).

In accordance with further embodiments, the magnetic lens 32 is displaceably coupled to the coil pad 20 so that the magnetic lens 32 can be moved relative to the coil pad 20 over time. This capability may be useful during treatment of an organ like the beating human heart, which is expanding and contracting over time. As the heart beats, the distance of the heart (at any given anatomical location) is moving away from and then toward the chest (i.e., body surface area). So in order to maintain a certain amount of energy being applied to the heart (i.e., so that it will not be high during diastole, when the heart is more closely to the chest, and then low, during systole, when the heart is moving away from the chest), movement of the magnetic lens 32 can be synchronized with the electrical activity of the heart (by monitoring electrical pulses on an ECG) to maintain a constant amount of electromagnetic energy over time at any given anatomical location despite being applied to a moving organ. In accordance with one implementation, the magnetic lens 32 may be movably coupled to a positioning frame that supports the coil pad 20. Motors may be provided for moving the magnetic lens 32 relative to the coil pad 20. For example, movement in a Z direction (i.e., toward and away from the heart) can be actuated by a miniature engine, thus causing the magnetic field to be modified over time in synchronism with the ECG.

One of many applications of the present invention is the application of WMF using a method and a device that can focus WMF and enable essential cardiac function recovery or activation of heart rhythm or heart contractile function in a patient. A primary object in such therapeutic applications is to use a planar array of coils to generate focused WMF so as to irradiate a target with effective radiation. In accordance with one aspect of the present invention, a focused WMF is transmitted to a patient's heart. This WMF is applied in a manner that causes beneficial effects on different tissues of the heart for any therapeutic purpose. In particular, the disclosed procedure can be applied for the purpose of enabling essential function recovery or activation in a subject to affect heart rhythm disturbances, or increase the contractile function of the heart by pulsing during the absolute refractory period of the ventricles, or at any other period of the cardiac cycle. It is also proposed to apply weak magnetic radiation for the purpose of treatment of hypertension by inducing peripheral arterial vasodilation. These examples however should not be interpreted as limiting the scope of treatment to the human heart only. Focused WMF can be employed in the treatment of biological tissue and organs other than the human heart.

The produced magnetic fields are alternating (i.e., modulated) and can be in the frequency of 0.1 Hz to 10 kHz, and their intensity can be less than approximately 10 microTesla. For therapeutic purposes, it is preferred to employ magnetic fields having a strength of 1 microTesla, with an AC frequency in the range of 2 to 64 Hz. The optimal frequency depends on the specific case, yet higher intensities of the magnetic field can be selected if needed. Adding the high-permeability alloy increases the magnetic field strength; however, with the same current source/battery voltage.

The affecting magnetic field pulses may optionally be synchronized with ECG events so as to select the specific period in the cardiac cycle when different tissues may depolarize or repolarize in succession, or in some abnormal way (such as during atrial depolarization, ventricular depolarization, ventricular repolarization, or the isoelectric period when the heart relaxes its ECG activity and its mechanical performance).

If required, a pharmacological agent may be administered adjunct to WMF treatment. Following administration of the pharmacological agent, the AC pulsed magnetic fields are subsequently applied, preferably via an external magnetic coil assembly or transducer.

In accordance with one embodiment, the coil pad is electrically coupled to a device comprising a current source in the form of a microprocessor or microcontroller powered by a battery. In addition, the ECG activity can be monitored by applying two or more ECG electrodes on the patient, which leads are connected directly to the microprocessor or microcontroller. When the microprocessor receives a signal representing a cardiac disturbance from the ECG electrode (s), such as a new onset of rhythm disturbance (rapid heart rate or partial, A-V block) the microprocessor, in accordance with pre-programmed instructions, will direct the magnetic field generator to emit focused weak magnetic fields for a period, intensity and frequency all predetermined by the microprocessor. The device can be powered by one 3-Volt battery or any other suitable battery.

Figure 6:
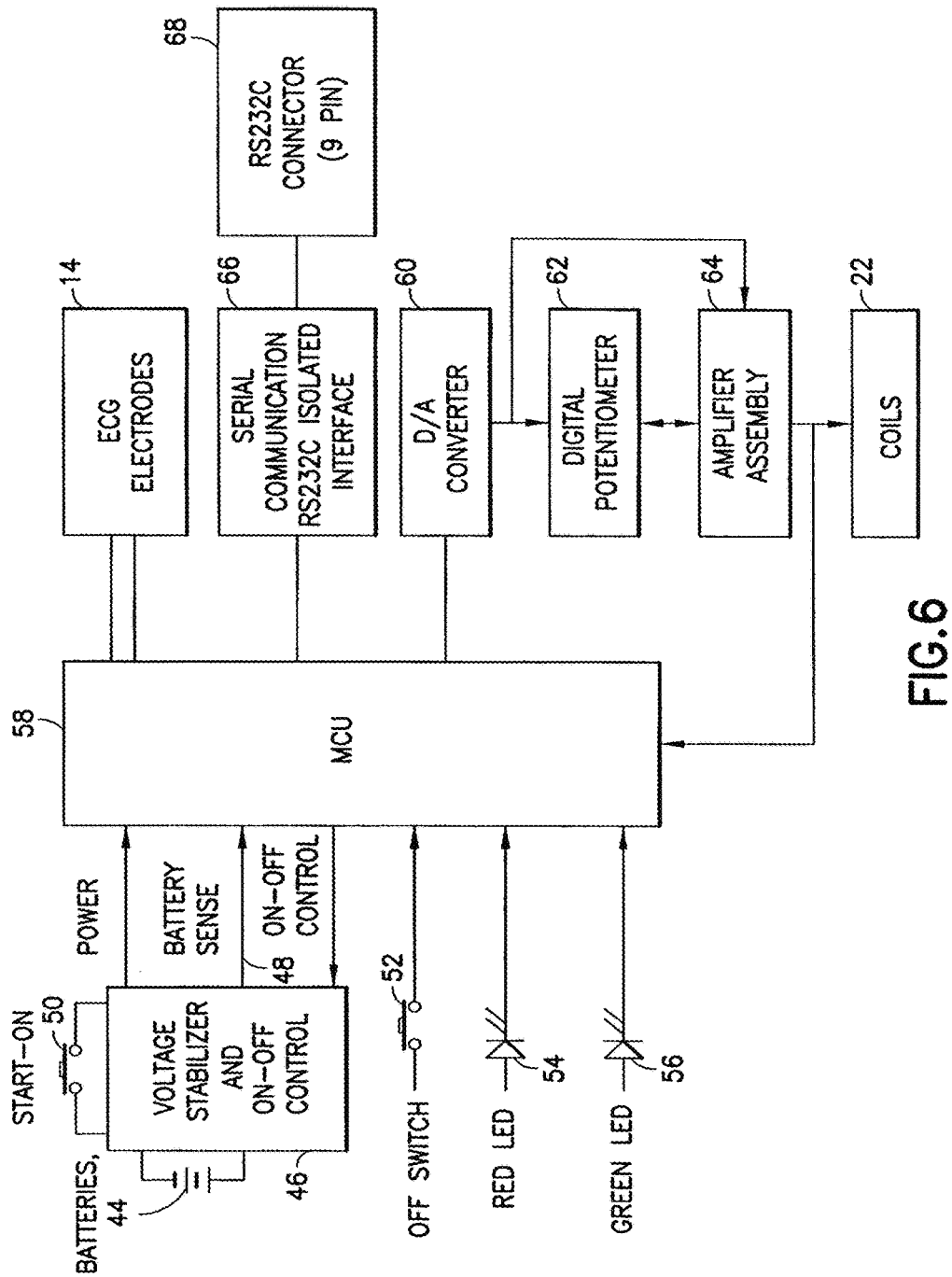
FIG. 6 is a block diagram representing circuitry incorporated in a magnetic wave generator in accordance with another embodiment of the invention.

FIG. 6 is a block diagram representing circuitry of a battery-powered radiation treatment device in accordance with one embodiment. This is a non-ionizing, non-heating electromagnetic field generator. The radiation treatment device comprises a microcontroller unit (MCU) 58 having an A/D input for coupling the radiation treatment device to an ECG electrode 14 attached to the chest of a patient. The microcontroller may be programmed with ECG analysis software for detecting predetermined points on the ECG waveforms acquired by the ECG electrode 14. The microcontroller 58 incorporates non-volatile memory (e.g., battery-powered memory, flash memory or other non-volatile memory technology) for storing also waveform/protocol parameters and other data received from a master or host computer. Such waveform/protocol parameters may include some or all of the following: gain, amplitude, frequency, waveshape, duration of treatment, time of treatment, number of times a treatment may be repeated, and other relevant functions, such as amplitude modulation, frequency modulation and phase modulation. These functions may be programmed to depend on the results of the ECG analysis. Alternatively, a microcomputer or microprocessor having similar functionality can be used.

The radiation treatment device depicted in FIG. 6 further comprises an RS232C communications channel, by means of which waveform parameters and treatment protocol data can be loaded into the radiation treatment device from a computer. The channel comprises serial communication RS232C isolated interface 66 and an RS232C 9-pin connector 68. In the alternative, a standard USB connection can be employed.

The microcontroller 58 processes the loaded treatment parameters and outputs a digital signal representing a waveform having a desired frequency and shape for driving the coils 22 of the magnetic field transducer. A digital-to-analog (D/A) converter 60 converts the digital signals output by the microcontroller 58 into an analog signal having the desired frequency and waveshape. The microcontroller 58 also outputs a digital value representing a setting to a digital potentiometer 62. The function of the digital potentiometer 62 is to adjust the level of the treatment signal, since the D/A converter 60 is always giving full amplitude. The output of the D/A converter 60 and the digital potentiometer 62 form the input signal to the amplifier assembly 64, the output of which is the current applied to the coils 22.

The microcontroller 58 outputs the digital waveform signals in accordance with the stored treatment protocol data. For example, the treatment protocol may comprise a single continuous treatment or a plurality of treatment cycles separated by quiescent intervals or rest periods.

Still referring to FIG. 6, the microcontroller 58 is powered by a battery or batteries 44. The voltage from the battery is supplied to the microcontroller 58 via a voltage stabilizer/on-off control circuit or chip 46. The voltage supplied by the battery is stabilized by the voltage stabilizer. The on-off control portion of chip 46 receives a control signal from the microcontroller 58. The treatment device can turn itself off by command from the microcontroller. The output of the analog chain (i.e., the D/A converter 60, the digital potentiometer 62 and the amplifier assembly 64) is connected into an A/D input of the microcontroller 58 to enable autotest of the proper operation of that subsystem. A Start-On pushbutton 50 is provided to turn the system on (after it is shut down). An Off pushbutton 52 is also provided for shutting down the system at any time. More precisely, the microcontroller 58 is programmed to send an Off command to chip 46 in response to pushbutton 52 being depressed. Optionally, the microcontroller can be programmed to take some other action in response to depression of pushbutton 52, in which case the latter could serve as a function switch in certain situations.

Numeral 48 indicates a low-voltage sense circuit that outputs an analog signal proportional to the current battery voltage to an input of the microcontroller 58. The microcontroller 58 incorporates an A/D converter that converts the analog signal to a digital value. That digital value is compared to a stored threshold value. When the battery voltage falls to a level corresponding to the stored threshold value, the microcontroller causes the red LED 54 to blink, indicating that the battery needs to be replaced. The red LED 54 is turned on as long as the radiation treatment device is activated. A green LED 56 is activated whenever the speaker is used and blinks when treatment is being performed. The green LED lights continuously for one minute after the end of treatment whenever number of available treatments remaining is either one or two.

The waveform parameters and treatment protocol data may be fed to the microcontroller 58 via the RS232C interface 66. Alternative communications channels can be employed. All parameters and protocol data are stored in a central computer and loaded into the radiation treatment device either directly or via a PC computer connected to the treatment device. The microcontroller 58 can store any desired waveform by receiving a series of values that can be repeatedly transmitted as an amplitude and time interval as selected by data transferred from the master computer. Alternatively, the microcontroller can have an internal algorithm to generate a waveform of the desired shape, amplitude and frequency to be supplied to the coils 22.

FIG. 7 is a diagram showing a front side of a flexible coil pad 20 comprising 138 spiral coils 22 in accordance with one implementation. FIG. 7A shows (on a magnified scale) the portion of the flexible coil pad 20 inside the dashed rectangular area 7A indicated in FIG. 7. The diameter of each spiral coil 22 is 12 mm. FIG. 8 is a diagram showing a back side of the flexible coil pad 20 depicted in FIG. 7. The spiral coils 22 are arranged in staggered columns. The spiral coils 22 in each column are electrically connected in series by short electrical conductors 28. The columns of spiral coils 22 are in turn electrically connected in series by long electrical conductors 26.

Figure 9:
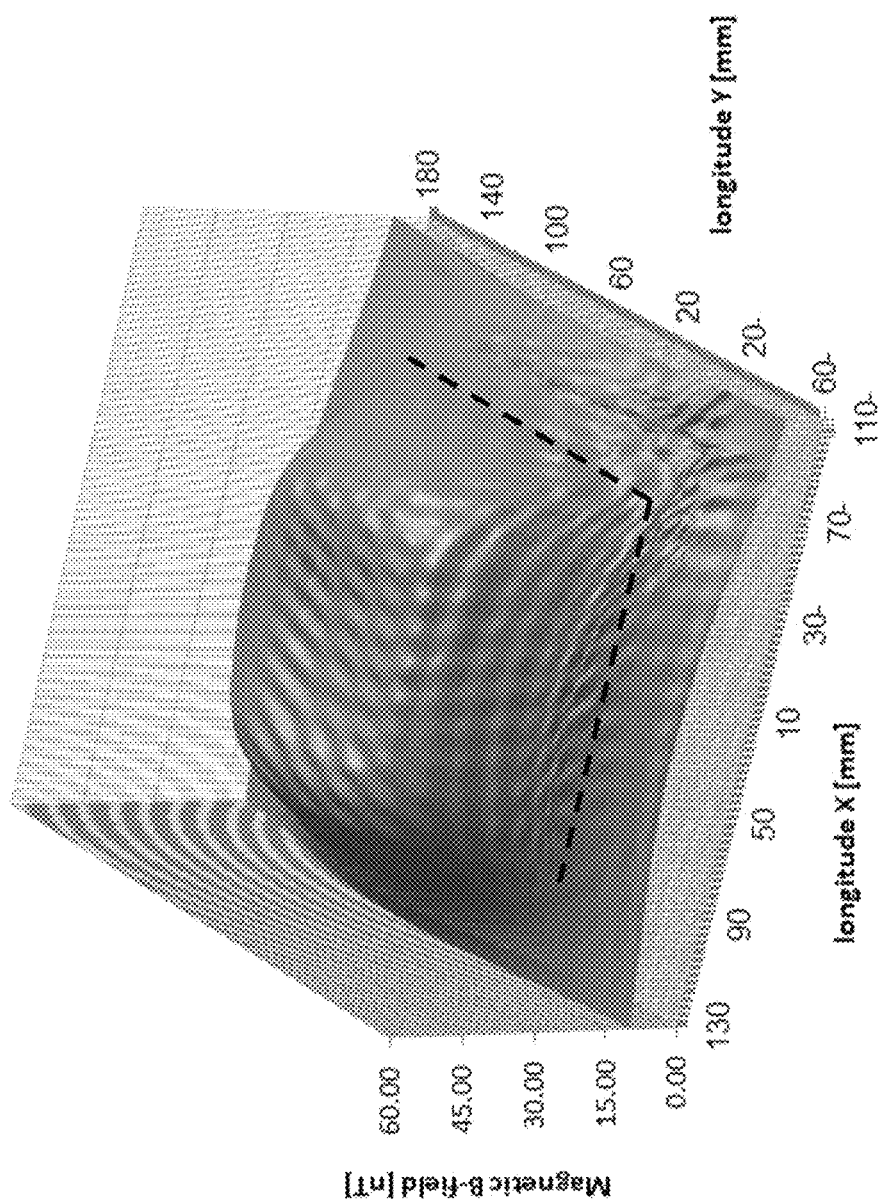
FIG. 9 is a graph showing the results of a three-dimensional simulation of the magnetic B-field at a distance of 40 mm from the flexible pad depicted in FIG. 7 when the pad coils are supplied with an electrical current (having a rectangular waveshape) of 7.5 mA.

FIG. 9 is a graph showing the results of a three-dimensional simulation of the magnetic B-field at a distance of 40 mm from the flexible pad depicted in FIG. 7 when electrical an electrical current (having a rectangular waveshape) of 7.5 mA flows through the pad coils. The shape of the magnetic field depicted in FIG. 9 can be sharpened and focused using one or more sheets of high-permeability material as disclosed above.

It should be appreciated that the magnetic field transducer need not be in the form of a planar array of spiral coils. The geometry of the coils may be varied (e.g., diamond-shaped, ring-shaped or square). Also the number, size, arrangement and spacing of the coils may be varied within wide limits so long as the total magnetic flux produced at the target depth is sufficient to provide a therapeutic stimulation, particularly in various regions within the heart such as the SA node, the atria, the left ventricular septum, etc. The apparatus disclosed herein is capable of applying weak magnetic fields in a focused region as small as few square centimeters.

Figure 10:
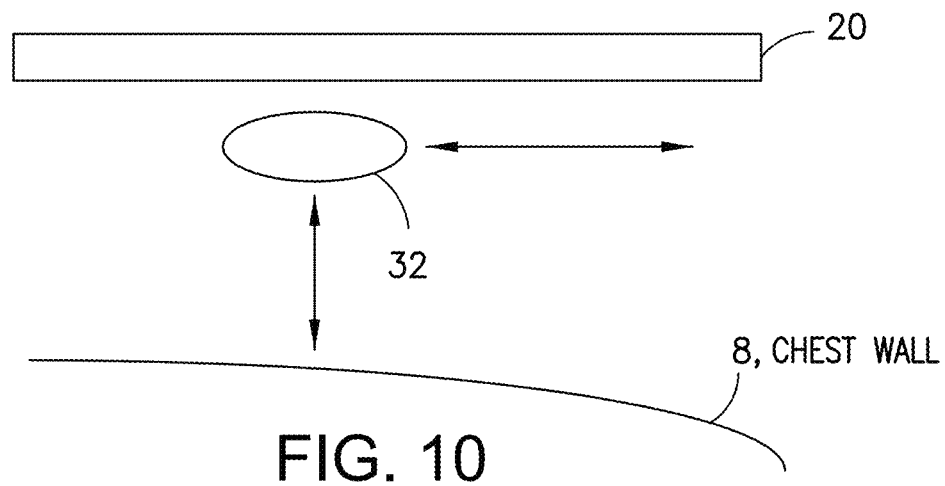
FIG. 10 is a diagram showing the placement of a disk made of high-permeability material between a coil pad and a chest of a patient.

FIG. 10 is a diagram showing the placement of a disk made of high-permeability material 32 between a coil pad 20 and a chest 8 of a patient. This apparatus can be used to stimulate confined regions (limited in area or depth) within the heart. Upon energization of the coils with electric current, the coils produce focused magnetic fields that are directed into the heart, and particularly into the area of interest (the atrium, ventricles) in the patient. Alternatively, the apparatus could be used to treat other portions of the human anatomy, such as other organs or tumors.

Patients who have chronic or new onset heart failure, or patients who were refractory to conventional therapy, are expected to benefit from the therapeutic treatment with weak magnetic fields. It will be imperative to fit variable properties of magnetic therapy to different cardiac arrhythmias, depending on their type and tissue (atrial, ventricular, A-V nodal, etc.). It is important to note that intracellular calcium overload facilitates cardiac dysrhythmias as well as compromising optimal cardiac function. The effect of weak magnetic fields to inhibit voltage-gate calcium channels is an important move in the right direction in combating hypertrophic cardiomyopathy and heart failure.

Figure 11:
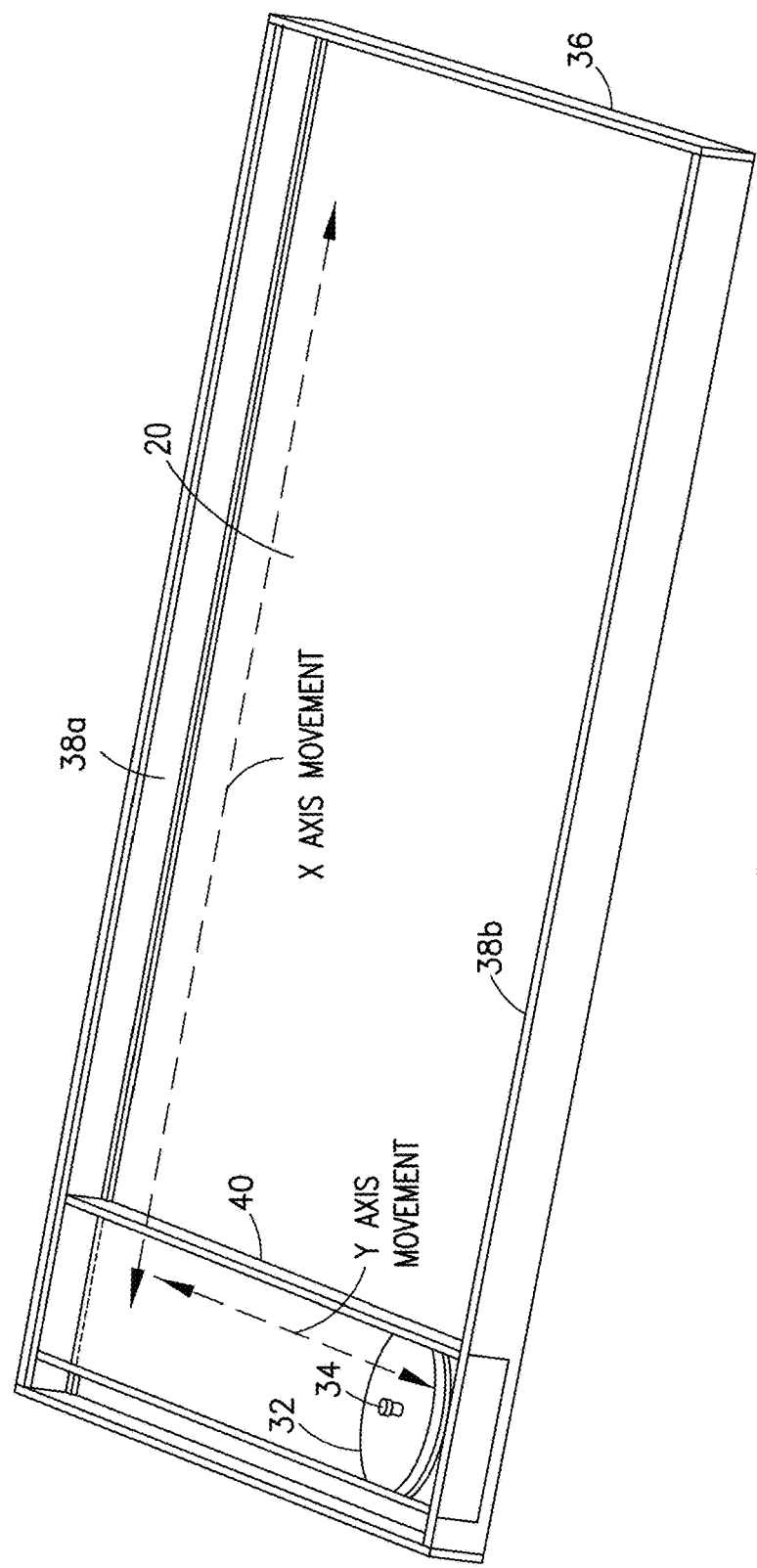
FIG. 11 is a diagram representing an isometric view of an apparatus comprising a coil pad assembled in a positioning mechanism that movably supports a disk made of high-permeability material in accordance with one embodiment. The dashed double-headed arrows respectively indicate that the disk is movable in X and Y directions relative to the coil pad.

FIG. 11 is a diagram representing an isometric view of an apparatus comprising a coil pad 20 assembled in a positioning mechanism that movably supports a magnetic lens 32 in the form of disk made of high-permeability material in accordance with one embodiment. The dashed double-headed arrows respectively indicate that the magnetic lens 32 is movable in X and Y directions relative to the coil pad 20.

Still referring to FIG. 11, the positioning mechanism comprises a rectangular frame 36 that supports a coil pad 20. A pair of tracks 38a and 38b (only track 38a is visible) are incorporated in or attached to opposite sides of the rectangular frame 36. The tracks 38a and 38b are parallel to an X direction. A sliding channel 40, extending in a Y direction, is slidably coupled to the tracks 38a and 38b to enable displacement of the channel 40 in an X direction. A magnetic lens 32 in the form of a disk made of high-permeability material is slidably disposed inside the channel 40 to enable displacement of the magnetic lens 32 in a Y direction.

Figure 12:
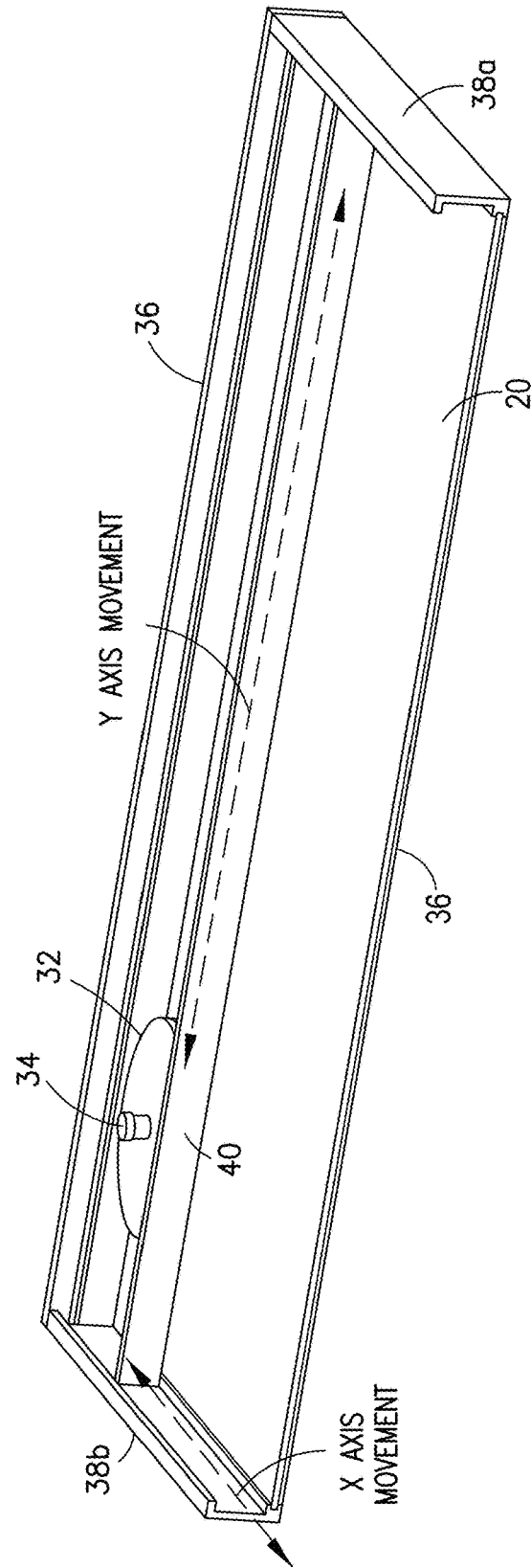
FIG. 12 is a diagram representing an isometric view of a portion of the apparatus depicted in FIG. 11 that includes a sliding channel in which the high-permeability disk is slidable. Again the dashed double-headed arrows respectively indicate that the high-permeability disk is movable in X and Y directions relative to the coil pad. The frame is shown in section.

FIG. 12 is a diagram representing an isometric view of a portion of the apparatus depicted in FIG. 11 that includes the uniaxially displaceable channel 40 along which the magnetic lens 32 is uniaxially displaceable. Again the dashed double-headed arrows respectively indicate that the magnetic lens 32 is movable in X and Y directions relative to the coil pad 20. The frame 36 is shown in section. A system technician can manually adjust the position of the magnetic lens 32 relative to the frame 36 by manipulation of a screw 34, as will be described in more detail below with reference to FIG. 14.

Figure 13:
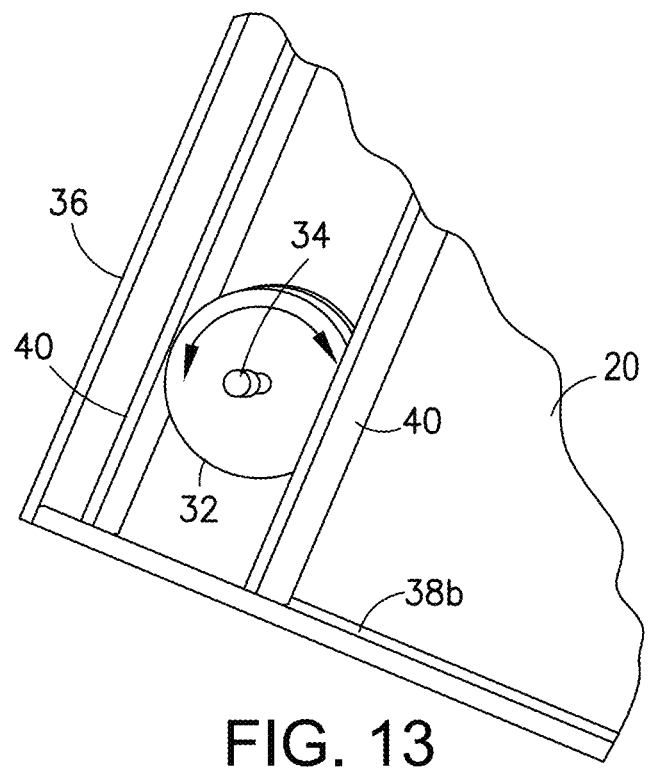
FIG. 13 is a diagram representing an isometric view on a magnified scale of a portion of the apparatus depicted in FIG. 11 that includes the high-permeability disk slidably installed in the sliding channel. The curved double-headed arrow indicates rotation of a screw/base disk assembly that supports the high-permeability disk.

FIG. 13 is a diagram representing an isometric view on a magnified scale of a portion of the apparatus depicted in FIG. 11 that includes the magnetic lens 32 slidably installed in the sliding channel 40. The curved double-headed arrow indicates rotation of the screw 24, which rotation has the effect of raising or lowering (depending on the direction of screw rotation) the magnetic lens 32 along a Z axis which is perpendicular to the X and Y axes depicted in FIG. 12

Figure 14:
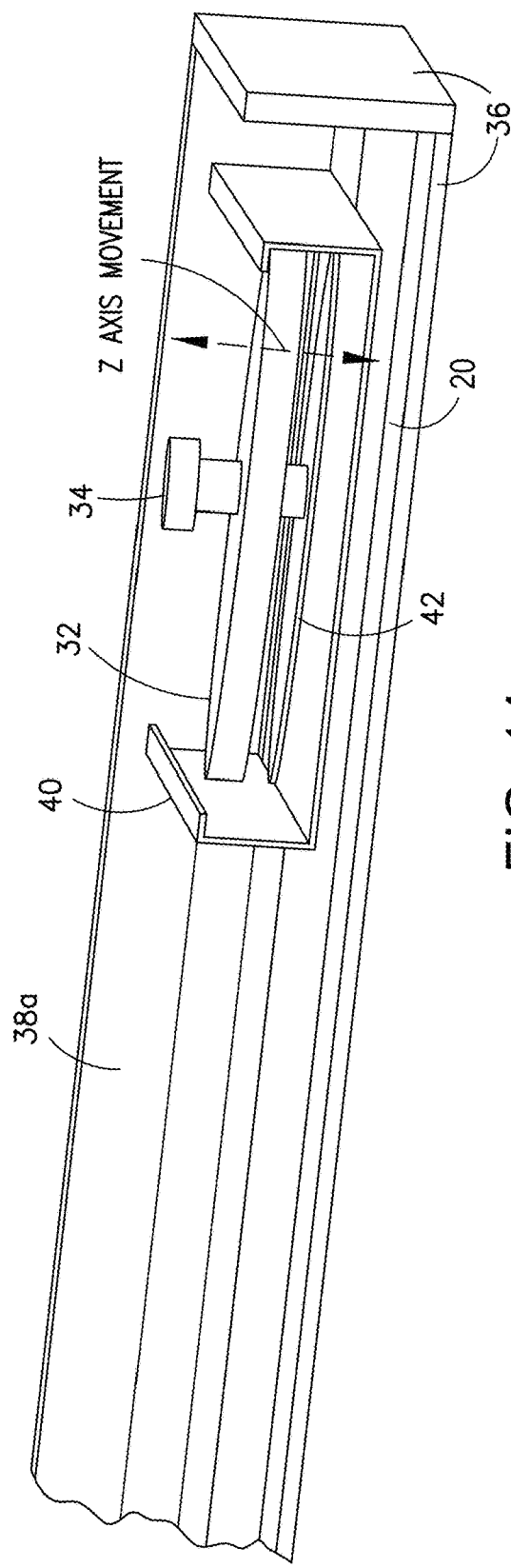
FIG. 14 is a diagram representing an isometric view of some components of the apparatus depicted in FIG. 11, including the sliding channel (shown in section), the high-permeability disk, the base disk and the screw. When the screw and base disk are rotated, the high-permeability disk is moved in a Z direction (indicated by the double-headed dashed arrow in FIG. 14).

FIG. 14 is a diagram representing an isometric view of some components of the apparatus depicted in FIG. 11, including the sliding channel 40 (shown in section), the magnetic lens 32, a base disk 42 and the screw 34 (the threads on the shaft of screw 34 are not shown). The distal end of the threaded shaft of screw 34 is attached to the center of the base disk 42. The magnetic lens 32 is threadably coupled to the threaded shaft of screw 34 so that when the screw/base disk subassembly is rotated, the magnetic lens 32 is moved up or down in a Z direction (indicated by the double-headed dashed arrow in FIG. 14). The assembly consisting of the screw/base disk subassembly and the magnetic lens 32 is slidably displaceable along the channel 40 in the Y direction. The channel 40 is displaceable along the frame 36 in the X direction. In this manner, the location of the magnetic lens 32 relative to the frame 36 can be adjusted in three dimensions by the system technician before the magnetic therapy treatment is started.

The apparatus disclosed herein is capable of applying WMF at an intensity selected to enable essential recovery of cardiovascular organ function or calcium accumulation, or relaxation of their exaggerated contractile function, to be effected on the heart or peripheral vascular system. This treatment may be applied for the purposes of normalizing cardiovascular function and alleviating such ailments as cardiac arrhythmias, diastolic heart failure and hypertension. The apparatus disclosed herein is also capable of applying WMF to other biological tissue and organs for other therapeutic purposes (e.g., cancer therapy).

While the invention has been described with reference to particular embodiments, it will be understood by those skilled in the art that various changes may be made and equivalents may be substituted for members thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the claims.

The invention claimed is:

1. An apparatus for treatment of a patient, comprising:
   a coil array comprising a multiplicity of coils made of electrically conductive material;
   a structure made of high-permeability material having a relative permeability value greater than 10,000, said structure being coupled to said coil array, positionable between the coils in the coil array and the patient, and movable relative to said coil array in X, Y and Z directions; and
   a current source coupled to said coils for supplying electrical current to said coils.

2. The apparatus as recited in claim 1, wherein said structure is a disk or a sheet.

3. The apparatus as recited in claim 2, wherein said structure is a sheet having a varying thickness.

4. The apparatus as recited in claim 1, wherein said coils are spiral coils connected in series.

5. The apparatus as recited in claim 1, wherein said high-permeability material is a nickel-iron alloy.

6. The apparatus as recited in claim 5, wherein said nickel-iron alloy has about 77% nickel.

7. The apparatus as recited in claim 5, wherein said nickel-iron alloy has about 80% nickel.

8. An apparatus for treatment of a patient, comprising:
   a coil array comprising a multiplicity of coils made of electrically conductive material;
   a structure made of high-permeability material having a relative permeability value greater than 10,000, said structure being coupled to said coil array and positionable between the coils in the coil array and the patient;
   a current source coupled to said coils for supplying electrical current to said coils; and
   a pad made of flexible plastic material, wherein said coils are printed on said pad.

9. A method of therapeutically treating biological tissue, comprising the following steps:
   placing an array of electrically conductive coils near a portion of a patient's body with an intervening high-permeability material having a relative permeability value greater than 10,000 coupled to the electrically conductive coils and positioned between the electrically conductive coils and the patient's body;

moving the high-permeability material relative to the array of electrically conductive coils to position the high-permeability material near the portion of the patient's body; and supplying said coils with an electrical current sufficient to cause said coils to generate a modulated magnetic field which is altered by the presence of the intervening high-permeability material.

10. The method as recited in claim 9, wherein the modulated magnetic field has a peak intensity less than 10 microTesla.

11. The method as recited in claim 9, wherein the frequency of the modulated magnetic field is about 16 Hz.

12. The method as recited in claim 9, wherein the generated magnetic field is focused by the high-permeability material.

13. The method as recited in claim 12, wherein the generated magnetic field is focused in a region of the patient's body.

14. A system for therapeutic treatment of a patient, comprising:
a magnetic field transducer for transducing electrical signals into magnetic fields;
a first sheet or disk made of high-permeability material having a relative permeability value greater than 10,000, said first sheet or disk being coupled to one side of said magnetic field transducer between the magnetic field transducer and the patient and movable relative to said magnetic field transducer in X, Y and Z directions; and
a current source coupled to said magnetic field transducer for supplying electrical current thereto,
wherein a first magnetic beam having a first profile is produced by the interaction of said first sheet or disk of high-permeability material with a magnetic field produced by said magnetic field transducer.

15. The system as recited in claim 14, further comprising a second sheet or disk made of high-permeability material, said second sheet or disk being interchangeable with said first sheet or disk, wherein a second magnetic beam having a second profile is produced by the interaction of said second sheet or disk of high-permeability material with the magnetic field produced by said magnetic field transducer, said second profile being different than said first profile.

16. The system as recited in claim 14, wherein said high-permeability material is a nickel-iron alloy.

17. The system as recited in claim 14, wherein said magnetic field transducer comprises an array of electrically conductive coils.

18. The system as recited in claim 14, further comprising a processor operatively coupled to a generator and programmed to provide parameter settings to said current source.

19. The system as recited in claim 14, wherein a location of said high-permeability material relative to said magnetic field transducer is adjustable in three dimensions.

* * * * *